US008066944B2

(12) United States Patent
Carter et al.

(10) Patent No.: US 8,066,944 B2
(45) Date of Patent: Nov. 29, 2011

(54) CHEMICAL SENSING DEVICE

(75) Inventors: Timothy Joseph Nicholas Carter, Sheppey (GB); Florence Colin, Canterbury (GB); Steven Andrew Ross, Ashford (GB); John Dalton Wright, Lincoln (GB)

(73) Assignee: Vivacta Limited, Sittingbourne, Kent (GB)

( * ) Notice: Subject to any disclaimer, the term of this patent is extended or adjusted under 35 U.S.C. 154(b) by 974 days.

(21) Appl. No.: 11/814,767

(22) PCT Filed: Jan. 24, 2006

(86) PCT No.: PCT/GB2006/000236
§ 371 (c)(1),
(2), (4) Date: Oct. 26, 2007

(87) PCT Pub. No.: WO2006/079795
PCT Pub. Date: Aug. 3, 2006

(65) Prior Publication Data
US 2008/0199970 A1     Aug. 21, 2008

(30) Foreign Application Priority Data

Jan. 25, 2005    (GB) .................................. 0501583.9

(51) Int. Cl.
    *G01N 15/06*      (2006.01)
    *G01N 21/00*      (2006.01)
    *G01N 25/20*      (2006.01)
    *G01N 21/75*      (2006.01)
    *C12M 1/34*      (2006.01)

(52) U.S. Cl. ....... 422/68.1; 422/400; 422/403; 422/430; 422/82.01; 422/82.05; 422/82.09; 436/147; 436/164; 436/166; 436/167; 436/172; 435/288.7

(58) Field of Classification Search .................. None
See application file for complete search history.

(56) References Cited

U.S. PATENT DOCUMENTS
4,007,009 A     2/1977    Wright et al.
(Continued)

FOREIGN PATENT DOCUMENTS
WO           9013017 A       11/1990
WO      2004090512 A1     10/2004

OTHER PUBLICATIONS

Colin, Florence, et al., "Modification of a piezo-optical gas dosimeter system towards continuous gas sensing: a feasibility study with carbon dioxide," Sensors and Actuators B 90: 216-221 (Apr. 20, 2003).

*Primary Examiner* — Jill Warden
*Assistant Examiner* — Neil N Turk
(74) *Attorney, Agent, or Firm* — Rothwell, Figg, Ernst & Manbeck, PC

(57) ABSTRACT

This invention relates to a chemical sensing device for detecting an analyte. The device comprises a light source; at least one luminescent reagent which is capable of luminescing when irradiated by the light source wherein the luminescence of the luminescent reagent is modifiable by the analyte thereby changing the generation of heat, which change in heat generation is proportional to the concentration of the analyte, a transducer having a pyroelectric or piezoelectric element and electrodes which is capable of transducing the change in heat to an electrical signal, and a detector which is capable of converting the electrical signal into an indication of the concentration of the analyte. The invention also relates to a method for detecting an analyte.

13 Claims, 1 Drawing Sheet

U.S. PATENT DOCUMENTS

| | | |
|---|---|---|
| 5,206,175 A | 4/1993 | Rossmann et al. |
| 6,402,369 B1 | 6/2002 | Ludington et al. |
| 2002/0173040 A1* | 11/2002 | Potyrailo et al. .................. 436/2 |
| 2005/0196322 A1* | 9/2005 | Truex et al. ................ 422/82.01 |

* cited by examiner

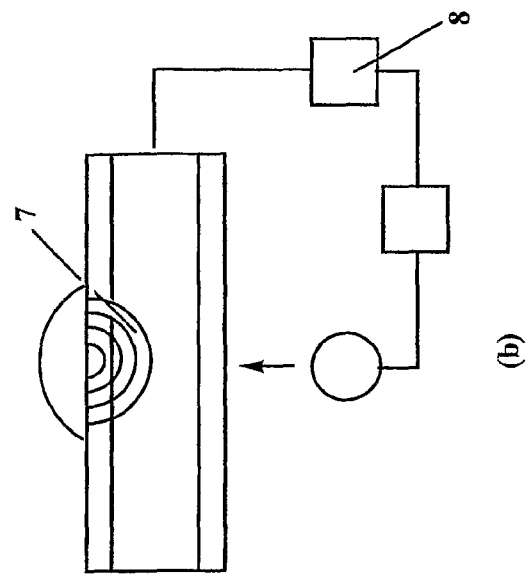
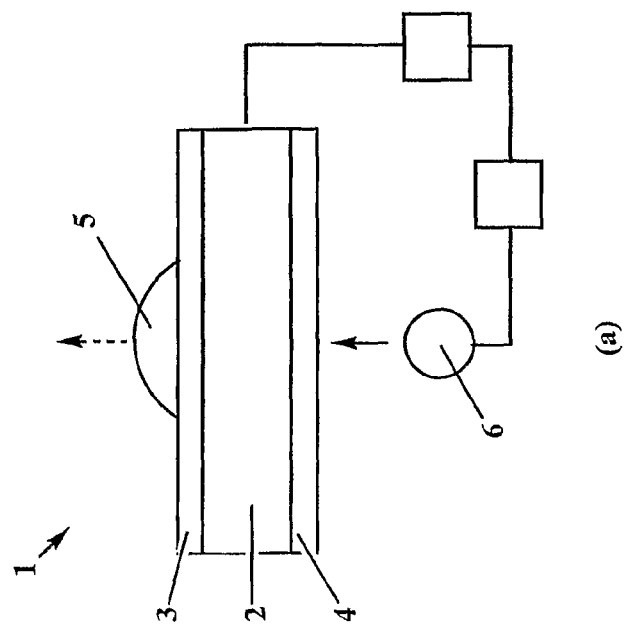
Figure

CHEMICAL SENSING DEVICE

This application is a 371 filing of PCT/GB2006/000236, filed Jan. 24, 2006, which claims priority from GB application 0501583.9, filed Jan. 25, 2005. These applications are incorporated herein by reference.

The present invention relates to a chemical sensing device and in particular to a chemical sensing device having a transducer and a luminescent reagent.

The monitoring of analytes, such as gases in the environment or biologically important compounds in bioassays, has a broad applicability. Accordingly, a wide variety of analytical and diagnostic devices are available. Many devices employ a reagent which undergoes an eye-detectable colour change in the presence of the species being detected. The reagent is often carried on a test strip and optics may be provided to assist in the measurement of the colour change.

WO 90/13017 discloses a pyroelectric or other thermoelectric transducer element in a strip form. Thin film electrodes are provided and one or more reagents are deposited on the transducer surface. The reagent undergoes a selective colorimetric change when it comes into contact with the species being detected. The device is then inserted into a detector where the transducer is illuminated from below by an LED light source and light absorption by the reagent is detected as microscopic heating at the transducer surface. The electrical signal output from the transducer is processed to derive the concentration of the species being detected. This type of system is typically formulated as a disposable badge clipped onto the clothing of the person being monitored together with a separate reader.

The system of WO 90/13017 is well suited for providing a history of exposure. In other words, the wearer of the badge is exposed to the species being detected and then, subsequently, the concentration of the species to which the wearer has been exposed is determined. However, while this system is useful in certain applications, it is difficult to provide a continuous measurement. This is a drawback where the wearer may be exposed to particularly hazardous species or, alternatively, if breathable oxygen levels are to be monitored.

A further drawback is that when the reagent becomes saturated, no further detection is possible.

This system is also restricted in the range of analytes which may be detected since only those undergoing a colour change on combination with the reagent are detectable.

Thus, there is a need for a chemical sensing device which avoids these drawbacks.

Accordingly, the present invention provides a chemical sensing device for detecting an analyte, comprising
a light source,
at least one luminescent reagent which is capable of luminescing when irradiated by the light source wherein the luminescence of the luminescent reagent is modifiable by the analyte thereby changing the generation of heat, which change in heat generation is proportional to the concentration of the analyte,
a transducer having a pyroelectric or piezoelectric element and electrodes which is capable of transducing the change in heat to an electrical signal,
a detector which is capable of converting the electrical signal into an indication of the concentration of the analyte.

Preferably the luminescence is quenchable by the analyte thereby increasing the generation of heat, which increase in heat generation being proportional to the concentration of the analyte.

Preferably the luminescence is enhancable by the analyte thereby decreasing the generation of heat, which decrease in heat generation being proportional to the concentration of the analyte.

Preferably the luminescent reagent is interconvertable between two chemical forms having different luminescence properties by reaction or combination with the analyte.

Preferably the luminescent reagent is mounted on the transducer.

Preferably the luminescent reagent is adsorbed on, entrapped within or immobilised upon a support material.

Preferably the luminescent reagent is a fluorescent reagent.

Preferably the chemical sensing device further comprises an additional reagent which is capable of reacting with a second analyte to change the local concentration of the first analyte thereby modifying the luminescence of the luminescent reagent to provide an indication of the concentration of the second analyte. Particularly preferably the first analyte is oxygen, the second analyte is glucose and the second reagent is glucose oxidase.

Preferably the luminescent reagent is a combination of a light-absorbing component and a luminescent component where the light-absorbing component absorbs light and then excites the luminescent component indirectly by energy transfer.

The present invention also provides a method for detecting an analyte, comprising irradiating at least one luminescent reagent,
exposing the luminescent reagent to a sample wherein, in the presence of the analyte, the luminescence is modified by the analyte thereby changing the amount of heat generated which change in heat generation is proportional to the concentration of the analyte,
transducing the change in heat to an electrical signal using a transducer having a pyroelectric or piezoelectric element and electrodes, and
converting the electrical signal into an indication of the concentration of the analyte.

Preferably the analyte quenches the luminescence of the luminescent reagent thereby increasing the generation of heat, which increase in heat generation being proportional to the concentration of the analyte.

Preferably the analyte enhances the luminescence of the luminescent reagent thereby decreasing the generation of heat, which decrease in heat generation being proportional to the concentration of the analyte.

Preferably the analyte converts the luminescent reagent from one chemical form to another chemical form where the two chemical forms have different luminescence properties.

Preferably a second reagent reacts with a second analyte to change the local concentration of the first analyte thereby modifying the luminescence of the luminescent reagent to provide an indication of the concentration of the second analyte.

The present invention will now be described with reference to the drawing, in which the FIGURE shows the chemical sensing device of the present invention (a) in the absence of an analyte and (b) in the presence of an analyte.

The present invention relies on the finding by the applicant that a modification in the luminescence of a luminescent reagent may be detected using a transducer which is capable of converting heat into an electrical signal. Such transducers are well known in the art. Preferably the transducer is a solid-state transducer. The luminescence may be modified in a number of ways, such as by luminescence quenching, luminescence enhancement, conversion of the luminescent reagent from a non- or weakly luminescent form to a luminescent form, or vice versa.

The FIGURE shows a chemical sensing device in accordance with an embodiment of the present invention which relies on luminescence quenching. FIGURE (a) represents the chemical sensing device 1 in the absence of the analyte. The device 1 comprises a pyroelectric or piezoelectric transducer 2 having electrode coatings 3,4. The pyroelectric transducer 2 is preferably a poled polyvinylidene fluoride film. The electrode coatings 3,4 are preferably formed from indium tin oxide having a thickness of about 35 nm or sputter-coated gold having a thickness of 5-15 nm. A luminescent reagent 5 is deposited, using any suitable technique, onto the upper electrode coating 3. The reagent may be in strip form and a plurality of reagents may be deposited. Preferably, the luminescent reagent 5 is absorbed on, entrapped within or immobilised upon a supporting material. Any suitable supporting material may be used, such as a polymer matrix, a porous glass or a sol-gel glass. A key feature of the present invention is that the luminescent reagent 5 luminesces when irradiated by a light source 6, such as an LED. The light source illuminates the reagent which then luminesces, indicated by a dashed arrow in FIGURE (a). The light source 6 is positioned so as to illuminate the reagent. Preferably, the light source 6 is positioned below the transducer 2 and electrodes 3,4 and the reagent 5 is illuminated through the transducer 2 and electrodes 3,4. In the absence of an analyte, radiative decay is favoured and hence little or no heat is generated.

In the presence of the analyte, as shown in FIGURE (b), the luminescence of the reagent 5 is quenched. This is indicated in FIGURE (b) by the absence of the dashed arrow. The luminescence quenching generates heat 7 which radiates into the pyroelectric or piezoelectric transducer 2. The applicant has found that the amount of heat 7 generated is proportional to the concentration of the analyte. The heat 7 generated by luminescence quenching stresses the pyroelectric or piezoelectric transducer 2 which generates an electric charge which, in turn, is detected by detector 8 using techniques known in the art. The detector 8 will then provide an indication of the amount of heat generated. This may be, for example, a concentration reading, an audible alarm etc. The detector must, of course, be calibrated before use using standard techniques.

In FIGURE (a) the reagent 5 luminesces on illumination by light source 6. Luminescence is a widely studied and well-understood phenomenon. The principle of luminescence is simple, the reagent molecule is in the ground state at room temperature (due to the Boltzmann distribution) and is excited to a higher energy level by radiation of a determined wavelength. Once the upper energy levels are populated, energy is released until the molecule is returned to its ground state. In luminescent molecules, this energy is re-emitted as light (radiative decay). In the reagent of the present invention, there is little or no heat transfer to the surroundings during luminescence. However, in the presence of the analyte (FIGURE (b)), the luminescence is quenched and the energy is released as heat rather than light (non-radiative decay). The magnitude of the quenching is proportional to the concentration of the analyte and, in turn, the magnitude of quenching is proportional to the amount of heat generated. This heat is converted to an electric signal by the transducer 2 which is detected by detector 8.

Alternatively, the interaction of the analyte with the luminescent reagent results in an enhancement (rather than quenching) in the luminescence. Thus, in the absence of the analyte (analogous to FIGURE (a)), the luminescent reagent is not luminescent or only weakly luminescent. Therefore, absorption of light by the non- or weakly luminescent reagent leads to excitation followed by non-radiative decay which generates heat. In the presence of the analyte (analogous to FIGURE (b)), luminescence is enhanced, i.e. favouring radiative decay, thereby reducing the amount of heat generated. This reduction in heat generation is converted into an electric signal by the transducer which is detected by the detector.

In another embodiment, the luminescent reagent exists in two chemical forms, a luminescent and a non- or weakly luminescent form. The luminescent reagent is converted from one form to the other by the analyte. Thus, for example, in one form the luminescent reagent luminesces in the absence of the analyte but in the presence of the analyte it is converted to the non- or weakly luminescent form. This modification in the luminescence is detected by the transducer/detector.

The luminescent reagent may be fluorescent or phosphorescent. However, fluorescent reagents are preferred.

The various factors affecting luminescence have been well researched and are well understood. In particular, a luminescent reagent must have a high quantum yield and have little or no overlap between absorption and emission. See, for example, "Principles of Fluorescence Spectroscopy" J. R. Lakowicz, 1999, Kluwer Academic/Plenum Press, New York.

There are many luminescent reagents known in the art which may be used in the chemical sensing device of the present invention. Typically, these reagents are metal complexes, (poly)aromatics and actinides.

Metal complexes luminesce due to metal to ligand charge transfer (MLCT) (d-d transitions are usually weak because they are forbidden). Accordingly, the ligand must be able to accept readily some electron density. The MLCT bands must also be of sufficiently high energy to make the radiative pathway statistically important. In addition, there should be no lower-lying d-d bands which can deplete the MLCT state and quench the emission. Thus, the crystal field splitting parameter, $\Delta_o$, should be large enough to place the d-d bands above the MLCT bands in the molecular orbital diagram. Finally, a high atomic number is preferred since spin-orbit coupling increases the likelihood of the radiative pathway, and spin-orbit coupling increases with atomic number.

Such a metal complex may be represented by the formula:

$M(L)_y$, where

M represents a metal ion of oxidation state I-IV of the 2nd or 3rd row of the d-block of the periodic table, and in particular Ru, Rh, Pd, Os, Ir or Pt, L represents a neutral or charged unidentate or polydentate ligand having a MLCT band of a lower energy than any of the metal ion d-d transitions and is capable of accepting electrons from the metal ion into the MLCT band and re-emitting the energy by a radiative pathway, and y is 1 to 6 and where y is greater than one the ligands may be the same or different.

Where the overall complex is charged, counterions are present. The counter ions are not material but should be selected to provide the required physical properties, such as solubility. Of course, the counter ions must not interfere with the fluorescence or quenching processes In order to luminesce, (poly)aromatics must have a HOMO-LUMO separation of an appropriate energy, have an allowable π-π* transition and be sufficiently rigid to inhibit non-radiative decay.

Actinides must have a large spin-orbit coupling and have organic chromophores, such as the ligands defined as "L" above, which readily sensitise the luminescence.

Clearly, the exact nature of the luminescent reagent is dependent on the nature of the analyte being monitored. In order to be detectable using the device and method of the present invention, the analyte must be capable of modifying the luminescence of the luminescent reagent.

The combinations of luminescent reagents and analytes which modify their luminescence are well known and hence appropriate luminescent reagents for use with a particular analyte may be chosen from the libraries of materials known in the art. Thus, it is unnecessary to provide an exhaustive list of chemical compounds herein. However, there follows a number of compounds which exemplify the luminescent reagent and analyte of the present invention.

The chemical sensing device of the present invention may be used to detect levels of oxygen. Molecular oxygen is known to quench the luminescence of a number of compounds. This is particularly important, for example, when the user of the device is working underground, such as in sewers.

Suitable luminescent reagents for monitoring oxygen include, for example, ruthenium trisbipyridyl complexes ($[Ru(bpy)_3]^{2+}$), fluoranthene, tetraphenylporphyrin and pyrene.

In the absence of oxygen, the $[Ru(bpy)_3]^{2+}$ complex fluoresces when excited at 470 nm with a blue LED. The excitation promotes a metal d-electron to a ligand $\pi^*$ orbital. Emission occurs from the MLCT bands, which lie lower in energy than the d-d band, themselves lower than the $\pi$-$\pi^*$ band. The energy gap is sufficient between the MLCT band and the ground state energy level for fluorescence to take place. The light absorbed is re-emitted and there is little or no heat transfer to the surrounding matrix and therefore no signal is obtained. In presence of oxygen, the fluorescence of the complex is quenched and energy is released as heat to the matrix. A signal can then be detected.

The concentration of ferrous ions in, say, groundwater may be determined using the present device employing Calcein Blue as the luminescent reagent. Calcein Blue (4-methylumbelliferone-8-methyleneiminodiacetic acid) fluoresces on excitation with light of an appropriate wavelength and this fluorescence is quenched by iron(II) ions. Accordingly, Calcein Blue is mounted on the transducer and fluorescence quenching by the iron(II) salt is detected by the change in heat due to fluorescence quenching. The fluorescence of H2tpp (5,10,15,20-tetraphenylporphyrin) is quenched in the presence of $Hg^{2+}$ ions and hence H2tpp may be used in the sensing device of the present invention to monitor the levels of toxic mercury salts in the environment.

The present device may also be used in biochemical assays. For example, bovine serum albumin (BSA) may be detected by employing Magdala Red (MR) as the fluorescent reagent. MR displays strong fluorescence on excitation at 348 nm and this fluorescence is quenched by BSA.

The device is also capable of detecting nitrated explosives or their residues. Nitrated explosives such as 2,4,6-trinitrotoluene (2,4,6-TNT), hexahydro-1,3,5-trinitro-1,3,5-triazine (RDX), octahydro-1,3,5,7-tetranitro-1,3,5,7-tetrazine (HMX), nitromethane and ammonium nitrate quench the fluorescence of polyaromatic hydrocarbons such as pyrene and hence may be used in the device of the present invention.

Di- or trinitrophenols may be detected based on fluorescence quenching of 3,3',5,5'-tetramethylbenzidine dihydrochloride (TMB-d). TMB-d emits strong fluorescence in the UV region. A non-fluorescent ground-state is formed by collisional deactivation by di- and trinitrophenols.

Numerous other examples of fluorescence quenching are known. For example, molecular oxygen quenches most fluorophores; amines quench unsubstituted aromatic hydrocarbons by charge transfer; indole, carbazole and derivatives thereof are uniquely sensitive to quenching by chlorinated hydrocarbons and by electron scavengers such as protons, histidine, cysteine, nitrate, fumarate, Cu(II), Pb(II), Cd(II) and Mn(II); indole, tryptophan and derivatives thereof are quenched by succinimide, dichloroacetamide, pyridinium hydrochloride, imidazolium hydrochloride, methionine, Eu(III), Ag(I) and Cs(I); FAD (flavin adenine dinucleotide) and NADH (reduced nicotinamide adenine dinucleotide) are quenched by adenine; biological quenching agents include purines, pyrimidines, and N-methyl nicotinamide; and xenon, hydrogen peroxide, acrylamide, perbromate ion, iodide ion, nitrous oxide, nitromethane, nitroxides, alkenes, sterically hindered saturated hydrocarbons and halogen-containing substances especially chloroform, trichloroethanol, bromobenzene and methylmercuric chloride are well-known quenching analytes.

Fluorescence enhancement (rather than quenching) may also be employed. Morin (2',3,4',5,7-pentahydroxyflavone) fluoresces weakly on excitation at 420 nm. However, this fluorescence is enhanced by the presence of $Al^{3+}$ ions. Accordingly, morin may be used in the device of the present invention to detect aluminium salts. Morin is mounted on the transducer and illuminated such that it fluoresces weakly. Accordingly, energy is emitted by non-radiative decay, i.e. heat is generated. In the presence of $Al^{3+}$ ions, fluorescence is enhanced (i.e. favouring radiative over non-radiative decay) thereby reducing the amount of heat generated. This reduction in heat generated is detected giving the concentration of $Al^{3+}$ ions.

The interconversion of luminescent and non- or weakly luminescent forms may also be employed.

For example, terbium(III) may be used to detect the local anaesthetics benzocaine and procaine. In the absence of these anaesthetics, terbium(III) produces no significant luminescence. However, these anaesthetics release p-aminobenzoic acid after a hydrolysis step in alkaline medium which reacts with the terbium(III) to give a luminescent chelate. Accordingly, in the absence of the hydrolysis product of the anaesthetics, absorption of light by the terbium(III) complex generates heat by non-radiative decay. In the presence of the hydrolysis product of the anaesthetics, absorption of light by the terbium(III) chelate provides luminescence and hence the heat generated is reduced. This reduction in heat is a function of the concentration of these anaesthetics present.

In another example, the luminescent reagent is a pH indicator in which the acid or base, but not both, is luminescent. On conversion to the non-luminescent form, absorption of light by the non-luminescent compound is detected as heat. The degree of conversion to the non-luminescent form may then be used to determine the pH of the sample being detected. A suitable reagent is. 1-hydroxypyrene-3,6,8-trisulphonate (HPTS).

Alternatively, the reagent is selected such that the luminescence is dependent on the local water content so that the device may be used to determine humidity.

Similarly, the luminescent reagent is a molecular receptor having a covalently attached fluorophore whose fluorescence efficiency changes depending on its position relative to the active cavity of the molecular receptor and which may be displaced from this active cavity by the analyte, for example, a dansyl group attached to β-cyclodextrin, whose fluorescence decreases in the presence of small hydrophobic molecules such as cyclohexane and toluene.

In the systems described above, luminescence is directly modified by the presence of the analyte species. Alternatively, luminescence modification may be used in conjunction with a secondary reaction to detect a second analyte (the "target" analyte) which does not itself directly modify the luminescence of the luminescent reagent to any significant extent. Instead, the second analyte reacts, or otherwise combines, with the first analyte or the luminescent reagent to affect the ability of the analyte to modify the luminescence.

For example, a detector for glucose employs the $[Ru(bpy)_3]^{2+}$/oxygen system as well as an additional reagent which reacts with glucose (the second analyte) to reduce the local oxygen concentration, e.g. glucose oxidase. The reduction in oxygen concentration is detected by the detector which, in turn, provides an indication of the amount of glucose present. Thus, the concentration of glucose in a sample is determined using fluorescence quenching of oxygen.

Alternatively, the second analyte reacts and produces a change in pH (for example, the urease-catalysed hydrolysis of urea to generate ammonia) and this change in pH is detected by the detector.

In another embodiment, the luminescent reagent is a combination of a light-absorbing component and a luminescent component where the light-absorbing component absorbs light and then excites the luminescent component indirectly by energy transfer. This energy transfer by the light-absorbing molecule is stimulated by the presence of the analyte. The light-absorbing molecule absorbs such light without energy transfer in the absence of the analyte, and hence gives no fluorescence, but. absorbs light with energy transfer in the presence of the analyte There are also a considerable number of bioassays which use changes in fluorescence as their method of detection. The present device particularly lends itself to use in immunoassays and nucleic acid-based assays.

In one form of immunoassay, an antibody is raised against the antigen which is to be measured. A fluorescent version of the antigen is also prepared, the fluorescence of which is quenched upon binding to the antibody. A sample which contains an unknown quantity of the unlabelled antigen being detected is then taken. All three components (antibody, labelled antigen and sample) are then mixed. If the sample contains a large amount of unlabelled antigen then this will mainly bind to the antibody and the labelled antigen will remain in solution, giving high fluorescence. Alternatively if there is very little antigen in solution, then the labelled antigen will bind to the antibody, leading to quenching of the fluorescence of the antigen. The degree of quenching is used as an indirect measure of the quantity of antigen (i.e. the analyte) in solution, using a previously prepared calibration curve. In the device of the present invention, the fluorescent antigen is mounted on the transducer.

Other variations on this type of assay are well known, see, for example, "The Immunoassay Handbook, 2nd Ed." David Wild, Ed., Nature Publishing Group, 2001.

Fluorescence modification is also well-known in the field of nucleic acid assays. One example is the SYBR Green dye which is used as a measure of double-stranded DNA. This dye fluoresces when bound to double-stranded DNA, but not when in free solution.

Real-time quantitative PCR with SYBR Green dye has been used to develop reliable and simple diagnostic assays for detecting genetic mutations, including duplications and deletions in mosquito drug-resistance genes, chromosomal translocations in human disease genes and base substitutions. It has also been used for the unequivocal identification of viral, bacterial or fungal pathogens. The method has also been used successfully for quantitative reverse-transcription PCR.

Other examples include "molecular beacons" which are oligonucleotide probes that emit fluorescence when hybridised to a target sequence of DNA or RNA. These probes undergo a conformational change when they hybridise to their target. See, for example, "Semiautomated clone verification by real-time PCR using molecular beacons" van Schie R C, Marras S A, Conroy J M, Nowak N J, Catanese J J, de Jong P J. Biotechniques 29, 1296-1300 (2000); "Multiplex detection of four pathogenic retroviruses using molecular beacons" Vet J A, Majithia A R, Marras S A, Tyagi S, Dube S, Poiesz B J, Kramer F R. Proc Natl Acad Sci USA 96, 6394-6399 (1999); and "Quantitative reverse transcription-polymerase chain reaction to study mRNA decay: comparison of endpoint and real-time methods" Schmittgen T D, Zakrajsek B A, Mills A G, Gorn V, Singer M J, Reed M W. Anal Biochem 285, 194-204 (2000).

The invention claimed is:

1. A chemical sensing device for detecting a first analyte, comprising
   a light source,
   at least one luminescent reagent which is capable of luminescing when irradiated by the light source wherein the luminescence of the luminescent reagent is modifiable by the first analyte thereby changing a generation of heat, which change in heat generation is proportional to the concentration of the first analyte,
   a transducer having a pyroelectric or piezoelectric element and electrodes which are capable of transducing the change in heat to an electrical signal, wherein the at least one luminescent reagent is deposited on at least one of the electrodes,
   a detector which is capable of converting the electrical signal into an indication of the concentration of the first analyte, and
   an additional reagent which is capable of reacting with a second analyte to change the local concentration of the first analyte thereby modifying the luminescence of the luminescent reagent to provide an indication of the concentration of the second analyte, wherein the additional reagent is deposited on at least one of the electrodes.

2. A chemical sensing device as claimed in claim 1, wherein the luminescence is quenchable by the first analyte thereby increasing the generation of heat, which increase in heat generation being proportional to the concentration of the first analyte.

3. A chemical sensing device as claimed in claim 1, wherein the luminescence is enhancable by the first analyte thereby decreasing the generation of heat, which decrease in heat generation being proportional to the concentration of the first analyte.

4. A chemical sensing device as claimed in claim 1, wherein the luminescent reagent is interconvertable between two chemical forms having different luminescence properties by reaction or combination with the first analyte.

5. A chemical sensing device as claimed in claim 1, wherein the luminescent reagent is mounted on the transducer.

6. A chemical sensing device as claimed in claim 1, wherein the luminescent reagent is adsorbed on, entrapped within or immobilised upon a support material.

7. A chemical sensing device as claimed in claim 1, wherein the luminescent reagent is a fluorescent reagent.

8. A chemical sensing device as claimed in claim 1, wherein the first analyte is oxygen, the second analyte is glucose and the second reagent is glucose oxidase.

9. A chemical sensing device as claimed in claim 1, wherein the luminescent reagent is a combination of a light-absorbing component and a luminescent component where the light-absorbing component absorbs light and then excites the luminescent component indirectly by energy transfer.

10. A method for detecting an analyte, comprising irradiating at least one luminescent reagent, exposing the luminescent reagent to a sample wherein, in the presence of the analyte, the luminescence is modified by the analyte thereby changing an amount of heat generated which change in heat generation is proportional to the concentration of the analyte, transducing the change in heat to an electrical signal using a transducer having a pyroelectric or piezoelectric element and electrodes, and converting the electrical signal into an indication of the concentration of the analyte, wherein a second reagent reacts with a second analyte to change the local concentration of the first analyte thereby modifying the luminescence of the luminescent reagent to provide an indication of the concentration of the second analyte.

11. A method as claimed in claim 10, wherein the analyte quenches the luminescence of the luminescent reagent thereby increasing the generation of heat, which increase in heat generation being proportional to the concentration of the analyte.

12. A method as claimed in claim 10, wherein the analyte enhances the luminescence of the luminescent reagent thereby decreasing the generation of heat, which decrease in heat generation being proportional to the concentration of the analyte.

13. A method as claimed in claim 10, wherein the analyte converts the luminescent reagent from one chemical form to another chemical form where the two chemical forms have different luminescence properties.

* * * * *